(12) United States Patent
Pariseau et al.

(10) Patent No.: US 9,157,847 B2
(45) Date of Patent: Oct. 13, 2015

(54) MIXED-MODE PHOTO-AMPLIFIER FOR PARTICLE COUNTER

(71) Applicant: Particles Plus, Inc., Canton, MA (US)

(72) Inventors: David Pariseau, Los Altos, CA (US); Ivan Horban, Grants Pass, OR (US)

(73) Assignee: Particles Plus, Inc., Stoughton, MA (US)

(\*) Notice: Subject to any disclaimer, the term of this patent is extended or adjusted under 35 U.S.C. 154(b) by 0 days.

(21) Appl. No.: 14/214,903

(22) Filed: Mar. 15, 2014

(65) Prior Publication Data

US 2014/0285801 A1 Sep. 25, 2014

Related U.S. Application Data

(60) Provisional application No. 61/786,626, filed on Mar. 15, 2013.

(51) Int. Cl.
*G01N 21/00* (2006.01)
*G01N 15/02* (2006.01)
*G01N 15/00* (2006.01)

(52) U.S. Cl.
CPC .... *G01N 15/0205* (2013.01); *G01N 2015/0046* (2013.01)

(58) Field of Classification Search
CPC .......... G01N 15/0205; G01N 15/0211; G01N 15/1459; G01N 2021/4716; G01N 15/1434
USPC .......................................................... 356/338
See application file for complete search history.

(56) References Cited

U.S. PATENT DOCUMENTS

| | | | | |
|---|---|---|---|---|
| 4,232,967 A * | 11/1980 | Grachev et al. | ............... | 356/336 |
| 4,506,678 A * | 3/1985 | Russell et al. | ............... | 600/536 |
| 6,788,152 B2 * | 9/2004 | Nishizono | ..................... | 330/308 |
| 2002/0135764 A1 * | 9/2002 | Oka et al. | ..................... | 356/338 |
| 2004/0068359 A1 * | 4/2004 | Neiss et al. | ..................... | 701/96 |
| 2006/0049815 A1 * | 3/2006 | Ho et al. | ....................... | 323/282 |
| 2006/0071803 A1 * | 4/2006 | Hamburger et al. | .......... | 340/630 |
| 2008/0215345 A1 * | 9/2008 | Hollingsworth et al. | ......... | 705/1 |
| 2011/0175661 A1 * | 7/2011 | Quesada et al. | .............. | 327/307 |

\* cited by examiner

*Primary Examiner* — Tarifur Chowdhury
*Assistant Examiner* — Md Rahman

(57) ABSTRACT

An airborne, gas, or liquid particle sensor with a mixed-mode photo-amplifier front-end. The photo-amplifier uses pulse-height for the high-gain channel and integrates the pulse-energy for the low-gain channel to provide for a larger dynamic range for larger size particles.

16 Claims, 2 Drawing Sheets

MIXED-MODE PHOTO-AMPLIFIER FOR PARTICLE COUNTER

CROSS-REFERENCE TO RELATED APPLICATION

This application claims priority to U.S. Provisional Application Ser. No. 61/786,626 filed on Mar. 15, 2013, titled MIXED-MODE PHOTO-AMPLIFIER FOR PARTICLE COUNTER by inventors David Pariseau and Ivan Horban, the entire disclosure of which is hereby incorporated herein by reference.

This application is related to and incorporates by reference U.S. Non-Provisional application Ser. No. 14/214,899, filed herewith on Mar. 15, 2014, titled PARTICLE COUNTER WITH INTEGRATED BOOTLOADER by inventor David Pariseau; U.S. Non-Provisional application Ser. No. 14/214,870, filed herewith on Mar. 15, 2014, titled PERSONAL AIR QUALITY MONITORING SYSTEM by inventors David Pariseau and Adam Giandomenico; U.S. Non-Provisional application Ser. No. 14/214,876, filed herewith on Mar. 15, 2014, titled MULTIPLE PARTICLE SENSORS IN A PARTICLE COUNTER by inventor David Pariseau; U.S. Non-Provisional application Ser. No. 14/214,889, filed herewith on Mar. 15, 2014, titled INTELLIGENT MODULES IN A PARTICLE COUNTER by inventor David Pariseau; U.S. Non-Provisional application Ser. No. 14/214,895, filed herewith on Mar. 15, 2014, titled PULSE SCOPE FOR PARTICLE COUNTER by inventor David Pariseau; and U.S. Non-Provisional application Ser. No. 14/214,907, filed herewith on Mar. 15, 2014, titled PULSE DISCRIMINATOR FOR PARTICLE COUNTER by inventors David Pariseau and Ivan Horban.

BACKGROUND

Particle counters have been used for decades in manufacturing or industrial applications to measure particulate quantities in air, gases or liquids. Typically such counters would also bin particulates by size. These size bins vary by application and often by instrument. A particle counter has at least one size channel and popular counters can have 6 or more channels. Typically these size channels discriminate pulses based on the pulse height of the incoming signal. The pulse height referring to the peak voltage of the signal.

However, such particle counters lack the dynamic range to detect particles with a wide range of particle sizes in one single instrument. Therefore, what is needed is a system and method for particle counting to detect a wider range of particle sizes within a single instrument.

SUMMARY

In accordance with the various aspects of the present invention, a system and method are provided for particle counting that detects a wider range of particle sizes. The foregoing is a summary and thus includes, by necessity, simplifications, generalizations and omissions of detail. Those skilled in the art will appreciate that the summary is illustrative only and is not intended to be in any way limiting.

BRIEF DESCRIPTION OF THE DRAWINGS

The foregoing summary as well as the following detailed description is better understood when read in conjunction with the appended drawings. For the purpose of illustrating the invention, there is shown in the drawings exemplary constructions of the invention; however, the invention is not limited to the specific various aspects, embodiments, methods and instrumentalities disclosed in the drawings.

DETAILED DESCRIPTION

Figure 1:
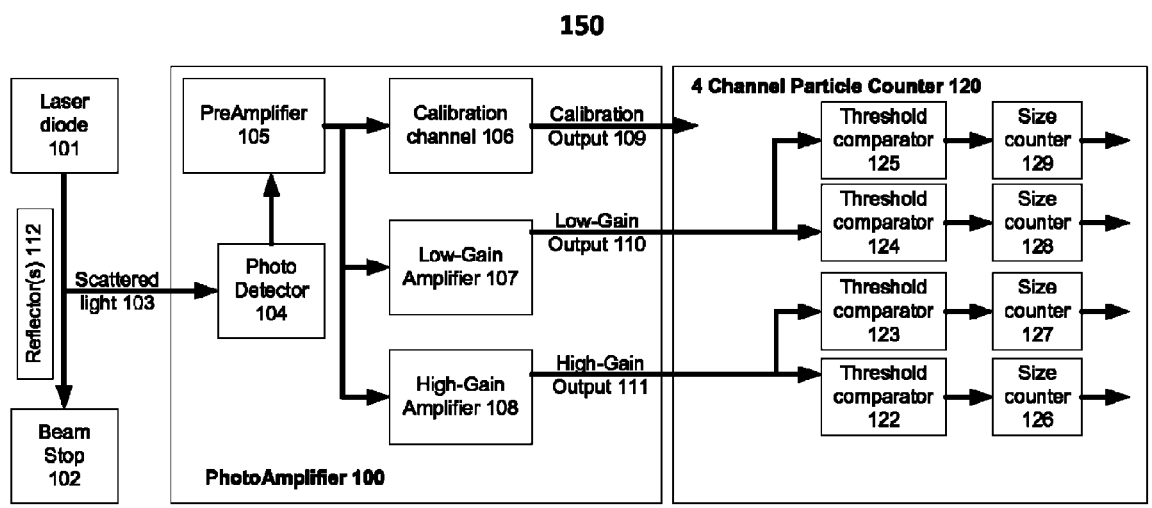
FIG. 1 shows a device in accordance with the various aspects of the present invention.

It is noted that, as used in this description, the singular forms "a," "an" and "the" include plural referents unless the context clearly dictates otherwise. Reference throughout this specification to "one aspect," "another aspect," "at least one aspect," "various aspects," "further aspect," "one embodiment," "an embodiment," "certain embodiments," or similar language means that a particular aspect, feature, structure, or characteristic described in connection with the embodiment or embodiments is included in at least one aspect or embodiment of the present invention. Thus, appearances of the phrases "in accordance with one aspect," "in accordance with various aspects," "in accordance another aspect," "one embodiment," "in at least one embodiment," "in an embodiment," "in certain embodiments," and similar language throughout this specification may, but do not necessarily, all refer to the same embodiment.

In accordance with the various aspects of the present invention, a device includes a computing device. As referred to herein, the devices may be part of a system or the system. It may be implemented to include a central processing unit (e.g., a processor), memory, input devices (e.g., keyboard and pointing devices), output devices (e.g., display devices), and storage device (e.g., disk drives). The memory and storage device are computer-readable media that may contain instructions or code that, when executed by the processor or the central processing unit, cause the device to perform certain tasks. In addition, data structures and message structures may be stored or transmitted via a data transmission medium, such as a signal on a communications link. Various communications channels may be used (e.g., the Internet, a local area network (LAN), a wide area network (WAN), or a point-to-point dial-up connection, or any other wireless channel or protocol) to create a link.

In accordance with the various aspects of the present invention, the device or system may be use various computing systems or devices including personal computers, server computers, hand-held or laptop devices, multiprocessor systems, microprocessor based systems, programmable consumer electronics, network personal computers (PCs), mini-computers, mainframe computers, distributed computing environments that include any of the above systems or devices, and the like. In accordance with the various aspects of the present invention, the device or system may also provide its services to various computing systems such as personal computers, cell phones, personal digital assistants, consumer electronics, home automation devices, and so on.

In accordance with the various aspects of the present invention, the device or system may be described in the general context of computer-executable instructions, such as program modules or code, which is executed by one or more computers or devices. Generally, program modules include routines, programs, objects, components, data structures, and so on that perform particular tasks or implement particular data types. Typically, the functionality of the program modules may be combined or distributed as desired in various embodiments.

Where a range of values is provided, it is understood that each intervening value, to the tenth of the unit of the lower limit unless the context clearly dictates otherwise, between the upper and lower limit of that range and any other stated or intervening value in that stated range, is encompassed within the aspects of the present invention. The upper and lower limits of these smaller ranges may independently be included in the smaller ranges and are also encompassed within the aspects of the present invention, subject to any specifically excluded limit in the stated range. Where the stated range includes one or both of the limits, ranges excluding either or both of those included limits are also included in the aspects of the present invention.

In accordance with the aspects and embodiments of the present invention, a photo-amplifier has multiple output gain stages in an attempt to capture a reasonable dynamic range for the size of interest. There is a difference in the amount of light scattered by a small, such as about a 0.1 um, particle and a much larger, such as a 100 um, particle. The scattered light is a function of wavelength whether or not the particle size is smaller or larger than the wavelength. For example, Table 1 gives comparative intensities for particles from about 0.1 um to about 100 um for a laser with a wavelength of about 650 nm. This yields 9 orders of magnitude across this range.

are sensitive to thermal variations, and vary from component to component, which results in a loss of accuracy and a drift over time.

In accordance with some aspects, adding output gain stages. By limiting the pre-amplifier gain-stage and then adding more output gain stages we can increase the dynamic range by using an output gain stage to supply the signals for only a few size channels. This design may need more hardware both in the photo-amplifier board and in the counter circuitry. It often means that the pre-amplifier gain is reduced in order not to saturate for the largest signal of interest. This means that the most sensitive signals (smallest particle channel) can suffer from excessive noise, due to the requiring most of the gain in the second channel.

Referring now to FIG. 1, a photo amplifier 100 and a four-channel particle counter 120 are shown as part of the system or device 150 in accordance with the various aspects and embodiments of the present invention. A beam present between the laser diode 101 and the beam stop 102 scatters light 103 as particles cross the beam. In accordance with one aspect of the present invention, the scattered light 103 is focused by one or more reflectors 112 onto the face of a photo detector or photo-diode 104, which is on the photo-amplifier 100. The tiny current in the photo-diode 104 is then pre-amplified by an amplifier 105, which is accordance with an aspect of the present invention is a trans-impedance amplifier.

In accordance with one aspect of the present invention, the

TABLE 1

| | Particle Diameter um | | | | | | | | | | |
|---|---|---|---|---|---|---|---|---|---|---|---|
| | 0.1 | 0.2 | 0.3 | 0.5 | 0.7 | 1 | 5 | 10 | 25 | 50 | 100 |
| Intensity Relative to 0.1 um Particles as 1 at 650 nm | 1.00E+00 | 6.40E+01 | 7.29E+02 | 1.56E+04 | 8.75E+04 | 1.79E+05 | 4.46E+06 | 1.79E+07 | 1.12E+08 | 4.46E+08 | 1.79E+09 |

For example, if a single gain-stage setting and 0.1 um particles were represented by a 1 mv peak signal (significantly below the noise floor), then the 100 um particles would require 1 million volts to display on a linear scale, which is well beyond reason for a sensor board. In accordance with the teachings of the present invention, to address this a number of techniques and compromises can be employed:

In accordance with some aspects, limit the number of range of channel sizes in a sensor. Some particle counters, also referred to as "particle counter system," allow a much narrower range of channels. Purchasers than choose a particle counter with channels sensitive to particles in a size range they are interested in. For example, a company might manufacture a 0.1 um to 0.5 um sensor; this would limit the dynamic range for to 4 orders of magnitude between the smallest and largest channels. However, this means that a potentially large number of sensor designs needs to be created, maintained, stocked, sold, and serviced, in order to handle the various size combinations. It also limits the ability of the purchaser to size particles outside of the size range of the device.

In accordance with some aspects, add gain compression circuitry. A particle counter includes non-linear elements to the feedback loop on the pre-amplifier stage. This element is very lightly engaged for the smallest signal, but has an increasing attenuation on the pre-amplifier output as the signal strength increases. These circuits can utilize diodes and transistors that have non-linear behavior across their range, signal from the amplifier 105 is available on a calibration channel 106 for use during calibration. The pre-amplifier 105 also sends a signal to one or more amplifiers. In accordance with various aspects and embodiments of the present invention there are two amplifiers: a low-gain amplifier 107 that produces signals on one channel, a low gain output 110, and a high-gain amplifier 108 that produces signals on another channel, a high-gain output 111. These amplifiers further increase the signal amplitude and transmit/send it to a particle counter 120.

At the particle counter 120 incoming signals are sorted into size bins. In accordance with some aspects and an embodiment of the present invention, there are four channels: two channels 122 and 123 are connected to the high-gain amplifier 108 at the output 111 and two channels 124 and 125 are connected to the low-gain amplifier 107 at the output 110. Threshold comparators 122, 123, 124, and 125 are setup during the calibration phase so that they each channel counts pulses above some threshold. In accordance with one aspect, this is a manual process with manual adjustment of a potentiometer. In accordance with another aspect, this is a programmatic process where firmware would set a digital potentiometer or digital-to-analog converter. The output of the comparators 122, 123, 124, and 125 are counter outputs 126, 127, 128, and 129, respectively, and are provided to or read by a microcontroller and displayed to the user through a display (not shown).

In accordance with other aspects of the present invention, the system functions for gases other than air as well as liquids.

In accordance with further aspects of the present invention, it also functions for counters that use a light-blocking rather than a light-scattering architecture, except that pulses in light-blocking systems see a decrease in light as the particles pass through the beam.

In accordance with certain aspects and embodiments, a mixed-mode pulse processing is used in the photo-amplifier 100 in order to provide a sensitive large dynamic range sensor with a fairly predictable and stable response; two gain outputs are used. The high-gain output is implemented normally, with the output representing the amplified trans-impedance output. The low-gain output has an output that is a function of the pulse-width of the saturated output of high-gain channel. If the optical design of the sensor block is such that larger particle sizes have a reasonably consistent pulse width by size in the high-gain channel, then such a function is used to compress a large variation in signal intensity into the available range of the gain output. A reasonable pulse-width distribution is accomplished by ensuring that the beam is a thin ribbon of constant power.

A variety of encoding techniques can be used. In certain embodiments, a capacitor is charged with a constant current during the pulse-width period. This yields a linear response for pulse-width, however since the signal intensity is non-linear and with the signal strength becomes very large near the largest particle sizes a non-linear encoding is used. In accordance with certain aspects and embodiments, a logarithmic amplifier is used to create the desired function. Here, a capacitor is charged during the pulse-width period. The capacitor charge curve is asymptotic and gives great resolution for the smaller particles and still provides some differentiation for the largest particle sizes and a very large dynamic range sensor is created.

Figure 2:
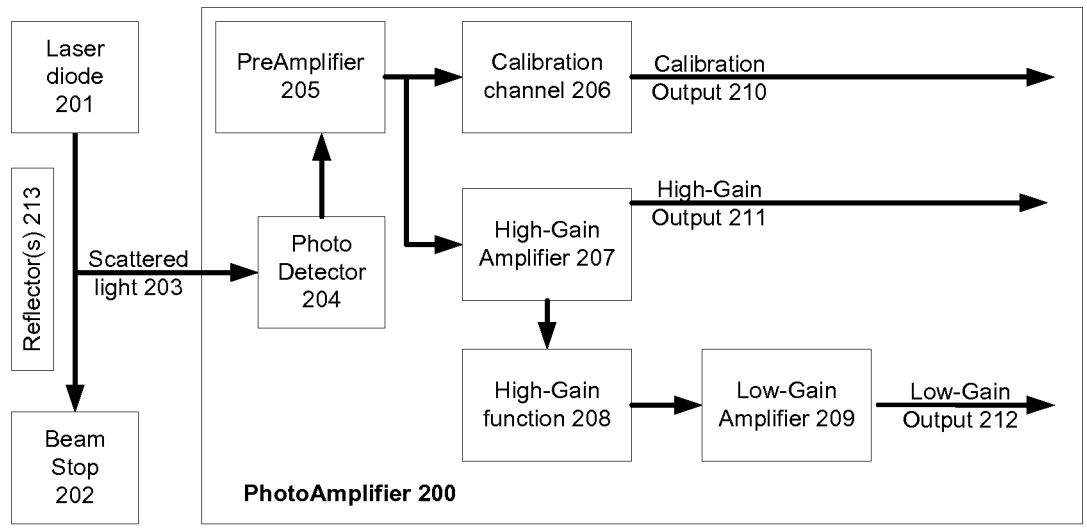
FIG. 2 shows a photo amplifier and FIG. 3 shows a high-gain function, also referred to as "high-gain device," both shown in accordance with the various aspects of the present invention.

Referring now to FIG. 2, in accordance with various aspects and embodiments of the present invention, a photo-amplifier 200 is shown. The photo-amplifier 200 includes a photo detector 204, a pre-amplifier 205 coupled to the photo detector 204; a high-gain amplifier 207 coupled to the pre-amplifier 205, a high-gain device coupled to the high-gain amplifier 207, and a low-gain amplifier 209 coupled to the high-gain device 208. The photo-amplifier 200 includes two gain outputs 211 and 212. In accordance with aspects of the present invention, the photo-amplifier 200 includes more gain outputs, while in accordance with other aspects, the photo-amplifier includes fewer gain outputs. In accordance with some aspects, the pre-amplifier 205 is a trans-impedance amplifier with a lot of gain and amplifies the incoming pulses in order for the smallest channel size to have a reasonable signal-to-noise ratio exiting at the high-gain amplifier 207, which has a high-gain output channel 211. The output from the high-gain amplifier 207 is used to control the high-gain function 208. The output of the high-gain function 208 provides an input for a channel that includes the low-gain amplifier 209. The low-gain amplifier produces an output on a low-gain output channel 212, which is based on the high-gain amplifier 207 pulse-width.

Figure 3:
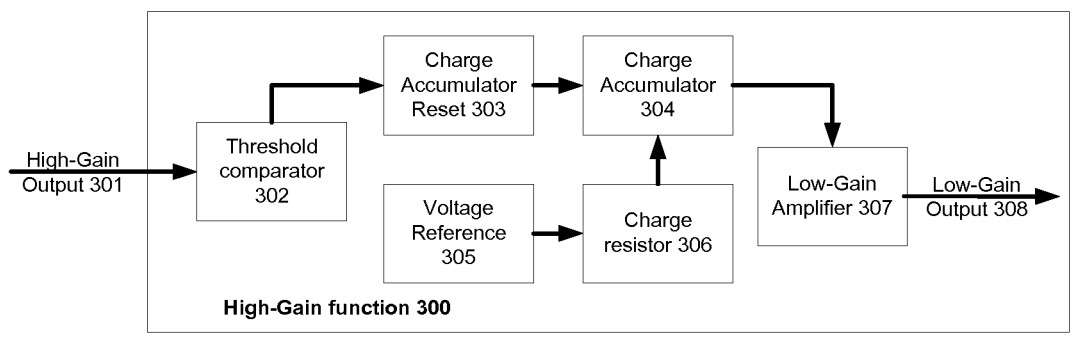

Referring now to FIG. 3, in accordance with various aspects of the present invention, a high-gain function or module 300, also referred to as "high-gain device," is shown. The high-gain function or module 300 includes and a low-gain amplifier 307 and a threshold comparator 302, which is used to measure the pulse-width for the high-gain output 301 (at some nominal voltage). The slopes, for saturated signals on the high-gain output 301 channel, are very steep and saturates. If the high-gain output 301 is below the level in a threshold comparator 302, then the charge accumulator reset 303 is enabled and a charge accumulator 304, which a precision capacitor, in this aspect of the present invention, is held shorted to ground. So, in that case the low-gain amplifier 307 has a low-gain output 308 that is low.

In accordance with some aspects of the present invention, when a pulse arrives on the high-gain output 301, the charge accumulator reset 303 is disabled. This allows the charge accumulator 304 to charge from the voltage reference 305 connected to it through the charge resistor 306. The capacitor or charge accumulator 304 charges according to a normal capacitor charge curve as a function of the capacitance of the charge accumulator 304 and the resistance of the voltage reference 305 and the charge resistor 306. Choosing the values for these components carefully allows dynamic range and resolution for the sensor to be adjusted and manipulated. The low-gain amplifier 307 follows the voltage across the charge accumulator 304 providing the scaled output on the low-gain output 308.

After the pulse on the high-gain output 301 drops once again below the value of the threshold comparator 302, the charge accumulator reset 303 is again enabled shorting the charge accumulator 304 to ground and drive the low-gain amplifier output 308 low.

In another aspect and embodiment, the charge resistor 306 is a digitally programmable potentiometer (or rheostat) and allows the dynamic range and resolution for the low-gain amplifier 307 to be adjusted dynamically during deployment of an instrument or during calibration of the instrument. This allows for more flexibility in addressing various dynamic ranges versus resolution trade-offs for specific instruments, and makes it possible for a single instrument or device using the same board to support a very wide range of possible applications. In certain aspects and embodiments, the low-gain output 308 is a function of a pulse-width of the high-gain amplifier 307.

In accordance with the various aspects of the present invention, the digitally programmable potentiometer also linearizes the output of larger particles on the low-gain output 308, making more effective use of the dynamic range and resolution for that output. The output has to be decoded appropriately by the particle counter. In accordance with some aspects of the present invention, the calibration phase typically records the size threshold based on actual particles introduced into the system, which means that no calculation is necessary for this process.

In accordance with aspects of the present invention, when a size bin is to be created, for a size that is not calibrated, the size bin can be interpolated between adjacent size bins, which are already calibrated, overlaid with the capacitor's characteristic charge curve in order to yield a reasonable approximation.

While various embodiments have been described above, it should be understood that they have been presented by way of example only, not limitation, and various changes in form and details may be made. Any portion of the device, instrument, apparatus and/or methods described herein may be combined in any combination, except mutually exclusive combinations. The aspects and embodiments described herein can include various combinations and/or sub-combinations of the functions, components and/or features of the different embodiments described. For example, multiple, distributed processing systems can be configured to operate in parallel.

Although the present invention has been described in detail with reference to certain embodiments, one skilled in the art will appreciate that the present invention can be practiced by other than the described embodiments, which have been presented for purposes of illustration and not of limitation.

Therefore, the scope of the appended claims should not be limited to the description of the embodiments contained herein.

It will be apparent that various aspects of the present invention as related to certain embodiments may be implemented in software, hardware, application logic, or a combination of software, hardware, and application logic. The software, application logic and/or hardware may reside on a server, an electronic device, or be a service. If desired, part of the software, application logic and/or hardware may reside on an electronic device and part of the software, application logic and/or hardware may reside on a remote location, such as server.

In accordance with the aspects disclosed in the teachings of the present invention and certain embodiments, a program or code may be noted as running on a device, an instrument, a system, or a computing device, all of which are an article of manufacture. Additional examples of an article of manufacture include: a server, a mainframe computer, a mobile telephone, a multimedia-enabled smartphone, a tablet computer, a personal digital assistant, a personal computer, a laptop, or other special purpose computer each having one or more processors (e.g., a Central Processing Unit, a Graphical Processing Unit, or a microprocessor) that is configured to execute a computer readable program code (e.g., an algorithm, hardware, firmware, and/or software) to receive data, transmit data, store data, or perform tasks and methods. Furthermore, an article of manufacture (e.g., device) includes a non-transitory computer readable medium having a series of instructions, such as computer readable program steps or code, which is encoded therein. In certain aspects and embodiments, the non-transitory computer readable medium includes one or more data repositories, memory, and storage, including non-volatile memory. The non-transitory computer readable medium includes corresponding computer readable program or code and may include one or more data repositories. Processors access the computer readable program code encoded on the corresponding non-transitory computer readable mediums and execute one or more corresponding instructions. Other hardware and software components and structures are also contemplated.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, representative illustrative methods and materials are described herein.

All publications and patents cited in this specification are herein incorporated by reference as if each individual publication or patent were specifically and individually indicated to be incorporated by reference and are incorporated herein by reference to disclose and describe the methods and/or system in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A particle counter system comprising:
    at least one airstream chamber;
    at least one light source focused into a beam that passes through the airstream chamber;
    at least one photo-detector within the airstream chamber, the photo-detector detects changes in light as airborne particulates pass through the beam;
    at least one high-gain amplifier in communication with the photo-detector, the high-gain amplifier converts signals from the photo-detector into amplified electrical pulses;
    at least one particulate size channel, where volume of air and light intensity are used in conjunction with the amplified electrical pulses to infer particulate counts for the particulate size channel; and
    at least one low-gain amplifier in communication with the high-gain amplifier which produces electrical pulses whose amplitudes are a function of a pulse-width of the high-gain amplifier.

2. The system in claim 1, wherein the output of the high-gain amplifier is a linear output based on the pulse-width of the high-gain amplifier's output.

3. The system in claim 2, further comprising a capacitor that is electrically connected to the high-gain amplifier's output, wherein the capacitor is charged through a fixed resistance.

4. The system in claim 2, further comprising a capacitor that is electrically connected to the high-gain amplifier's output, wherein the capacitor is charged through a variable resistance.

5. The system in claim 2, further comprising a capacitor that is electrically connected to the high-gain amplifier's output, wherein the capacitor is charged through a programmable resistance.

6. The system in claim 2, further comprising a capacitor that is electrically connected to the high-gain amplifier's output, wherein the capacitor is charged from a precision voltage source.

7. The system in claim 1, wherein the output of the high-gain amplifier is based on a capacitor charged as a function of the pulse-width of the high-gain amplifier's output.

8. The system in claim 7, wherein a size threshold, which is associated with a particle size not calibrated for, is determined using the capacitor's characteristic charge curve and at least two other calibration points.

9. A particle counter system comprising:
    at least one liquid chamber;
    at least one light source focused into a beam that passes through the liquid chamber;
    at least one photo-detector within the liquid chamber, the photo-detector detects changes in light as airborne particulates pass through the beam;
    at least one high-gain amplifier in communication with the photo-detector, the high-gain amplifier converts signals from the photo-detector into amplified electrical pulses;
    at least one particulate size channel, where volume of air and light intensity are used in conjunction with the amplified electrical pulses to infer particulate counts for the particulate size channel; and
    at least one low-gain amplifier in communication with the high-gain amplifier which produces electrical pulses whose amplitudes are a function of a pulse-width of the high-gain amplifier.

10. The system in claim 9, wherein the output of the high-gain amplifier is a linear output based on the pulse-width of the high-gain amplifier's output.

11. The system in claim 10, further comprising a capacitor that is electrically connected to the high-gain amplifier's output, wherein the capacitor is charged through a fixed resistance.

12. The system in claim 10, further comprising a capacitor that is electrically connected to the high-gain amplifier's output, wherein the capacitor is charged through a variable resistance.

13. The system in claim 10, further comprising a capacitor that is electrically connected to the high-gain amplifier's output, wherein the capacitor is charged through a programmable resistance.

14. The system in claim 10, further comprising a capacitor that is electrically connected to the high-gain amplifier's output, wherein the capacitor is charged from a precision voltage source.

15. The system in claim 9, wherein the output of the high-gain amplifier is based on a capacitor charged as a function of the pulse-width of the high-gain amplifier's output.

16. The system in claim 15, wherein a size threshold, which is associated with a particle size not calibrated for, is determined using the capacitor's characteristic charge curve and at least two other calibration points.

\* \* \* \* \*